United States Patent [19]
TenHoff et al.

[11] Patent Number: 5,842,994
[45] Date of Patent: Dec. 1, 1998

[54] MULTIFUNCTION INTRALUMINAL ULTRASOUND CATHETER HAVING A REMOVABLE CORE WITH MAXIMIZED TRANSDUCER APERTURE

[75] Inventors: Harm TenHoff, Mountain View, Calif.; Isaac Ostrovsky, Wellesley, Mass.; James D. Koger, Santa Cruz, Calif.

[73] Assignee: Boston Scientific Technology, Inc., Maple Grove, Minn.

[21] Appl. No.: 886,882

[22] Filed: Jul. 2, 1997

[51] Int. Cl.$^6$ .................................................. A61B 8/00
[52] U.S. Cl. ................................. 600/466; 600/468
[58] Field of Search ................................ 600/466, 467, 600/471, 468

[56] References Cited

U.S. PATENT DOCUMENTS

| | | | |
|---|---|---|---|
| 5,190,045 | 3/1993 | Frazin | 600/468 |
| 5,219,335 | 6/1993 | Willard et al. | 600/466 |
| 5,240,003 | 8/1993 | Lancee et al. | 600/467 |
| 5,240,437 | 8/1993 | Christain | 600/467 |
| 5,435,314 | 7/1995 | Dias | 600/467 |
| 5,454,373 | 10/1995 | Koger et al. | 600/467 |
| 5,485,854 | 1/1996 | Verdonk et al. | 600/467 |

*Primary Examiner*—Marvin M. Lateef
*Assistant Examiner*—Maulin Patel
*Attorney, Agent, or Firm*—Lyon & Lyon LLP

[57] ABSTRACT

A multi-function intraluminal ultrasound catheter assembly includes an axially disposed lumen having at least a first portion with a flat inner wall forming a "D-shaped" cross-section. An acoustic imaging window having a circular cross-section is connected to a distal end of the catheter assembly, wherein the cross-sectional dimension of the D-shaped portion of the lumen that extends from the flat inner wall is less that the available inner diameter of the imaging window. A flexible drive-shaft extends through the lumen and is connected to a transducer housing disposed in the acoustic imaging window area, the transducer housing having a substantially "D-shaped" outer perimeter, wherein the drive-shaft and connected transducer housing may thereby be retracted from the catheter assembly by first rotating the transducer housing until its D-shaped outer perimeter is substantially oriented with the D-shaped cross-section of the lumen. In a preferred embodiment, the transducer housing also includes a longitudinally disposed transducer mounting section configured such that the active surface of a transducer mounted therein is generally aligned across the maximal inner diameter of the acoustic imaging window.

15 Claims, 13 Drawing Sheets

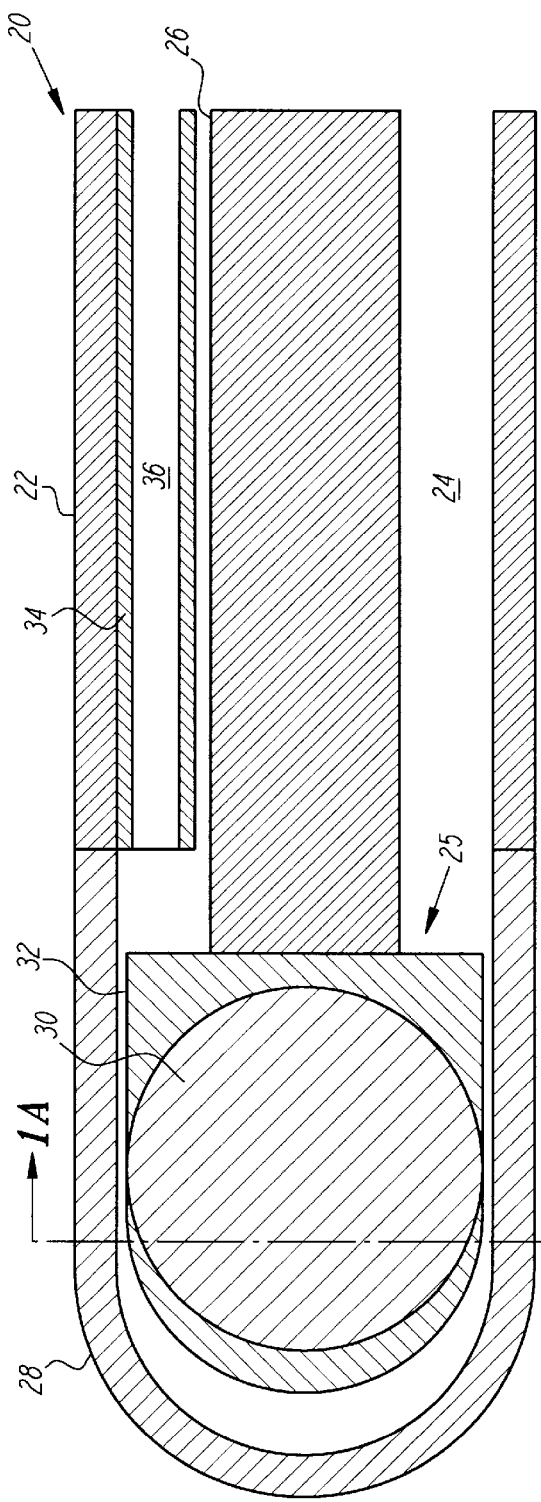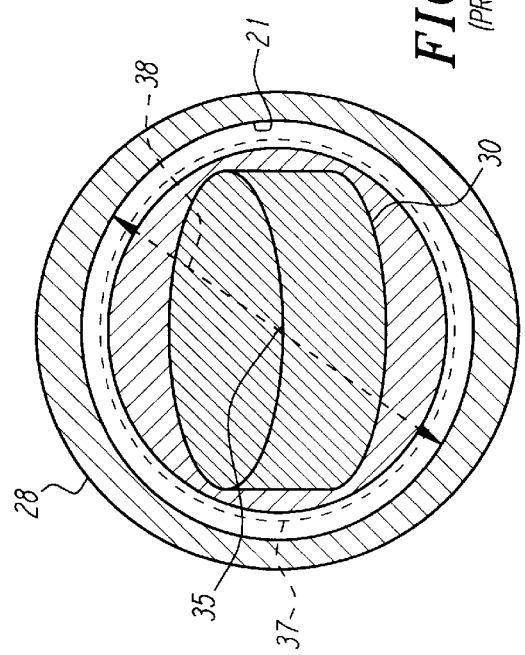
FIG. 1
(PRIOR ART)
FIG. 1A
(PRIOR ART)

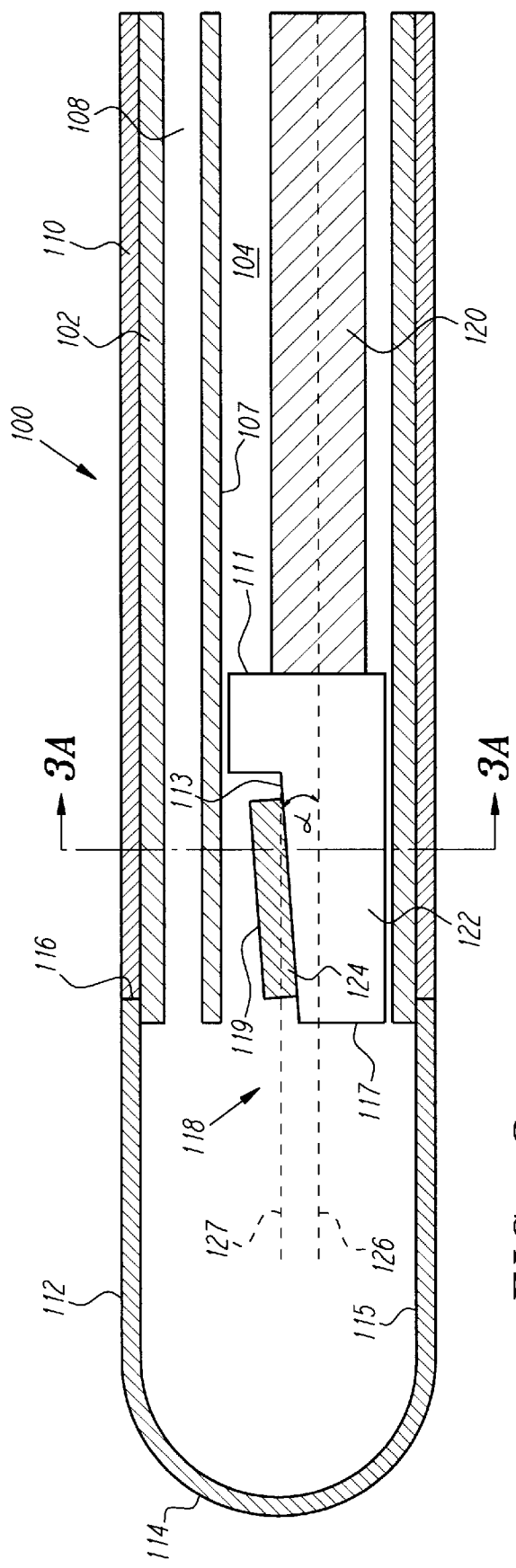
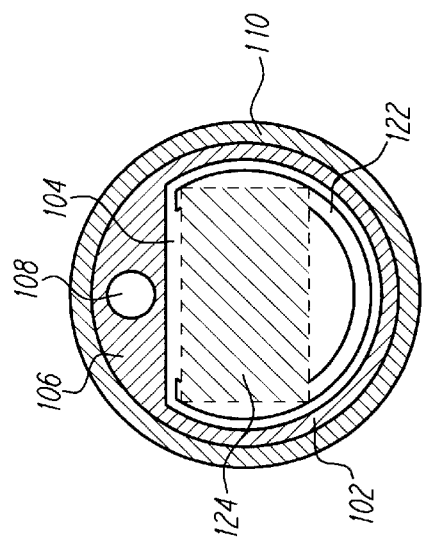
FIG. 3
FIG. 3A

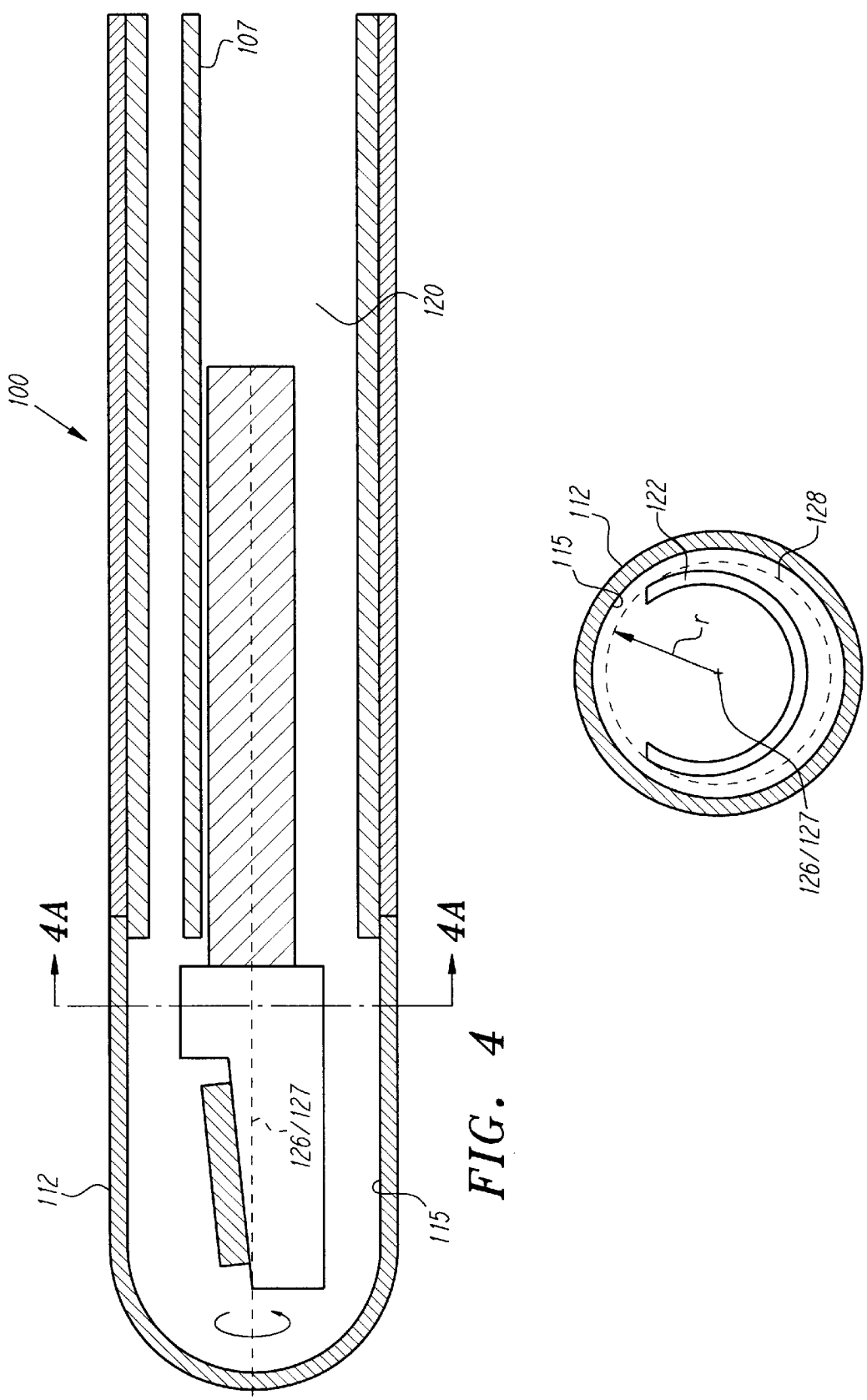

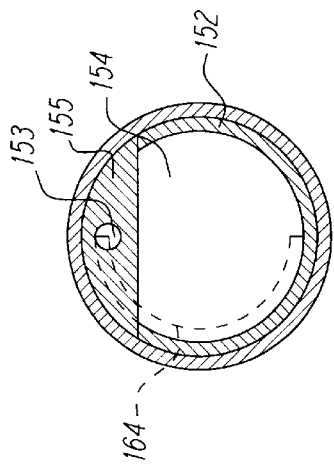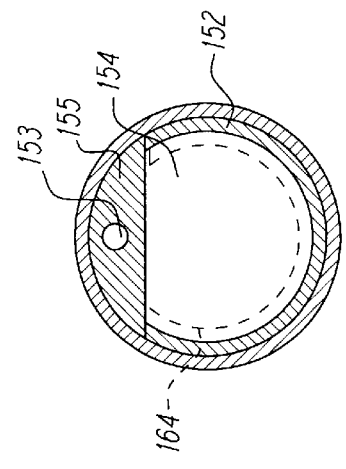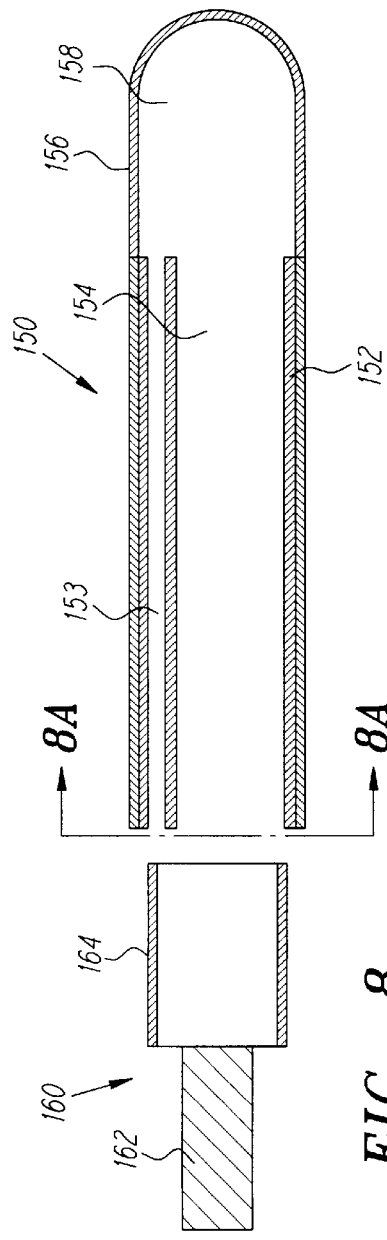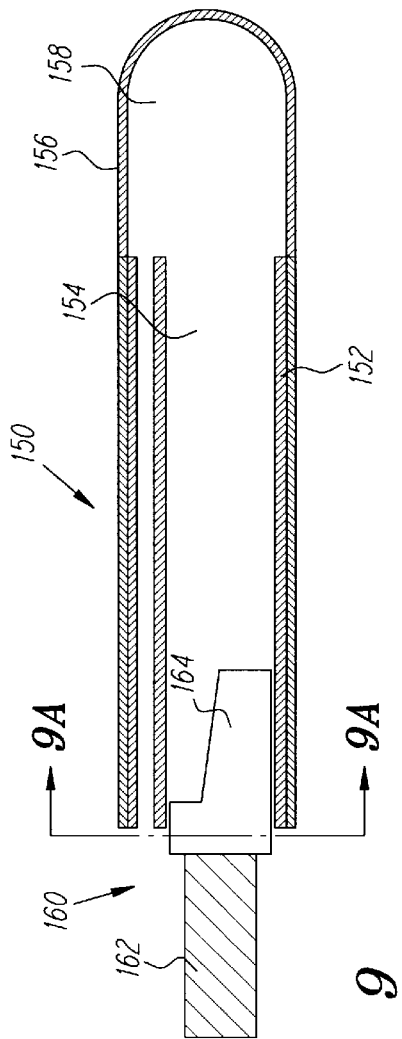

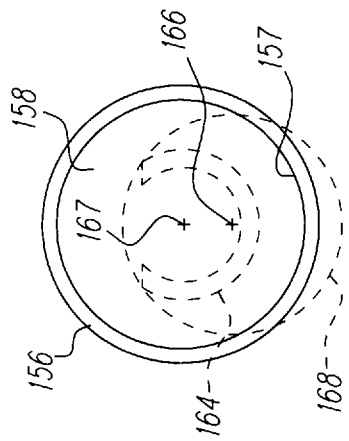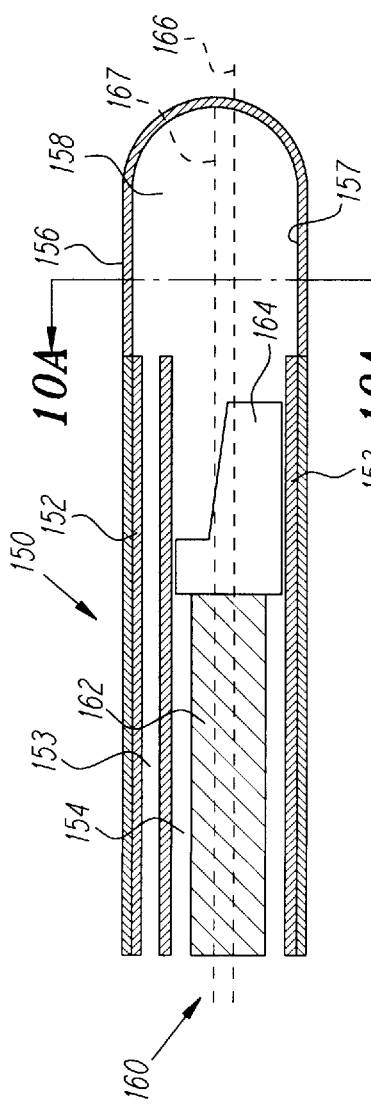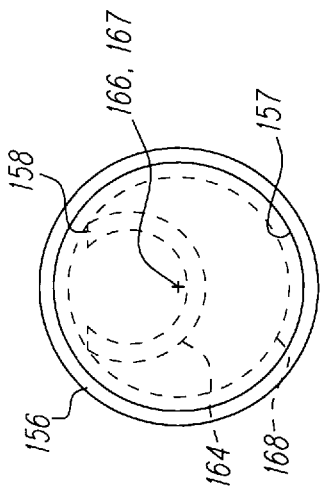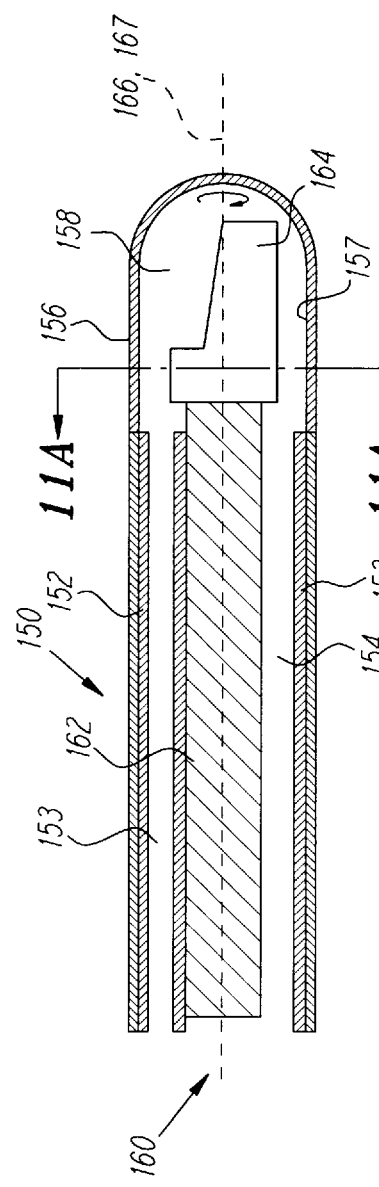

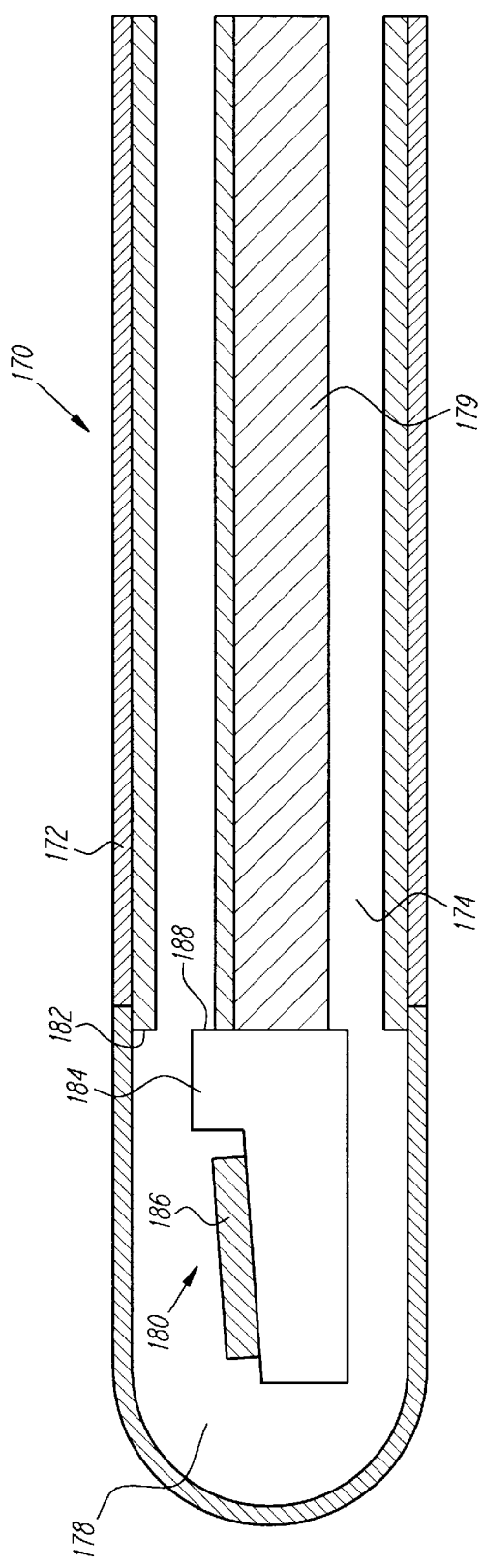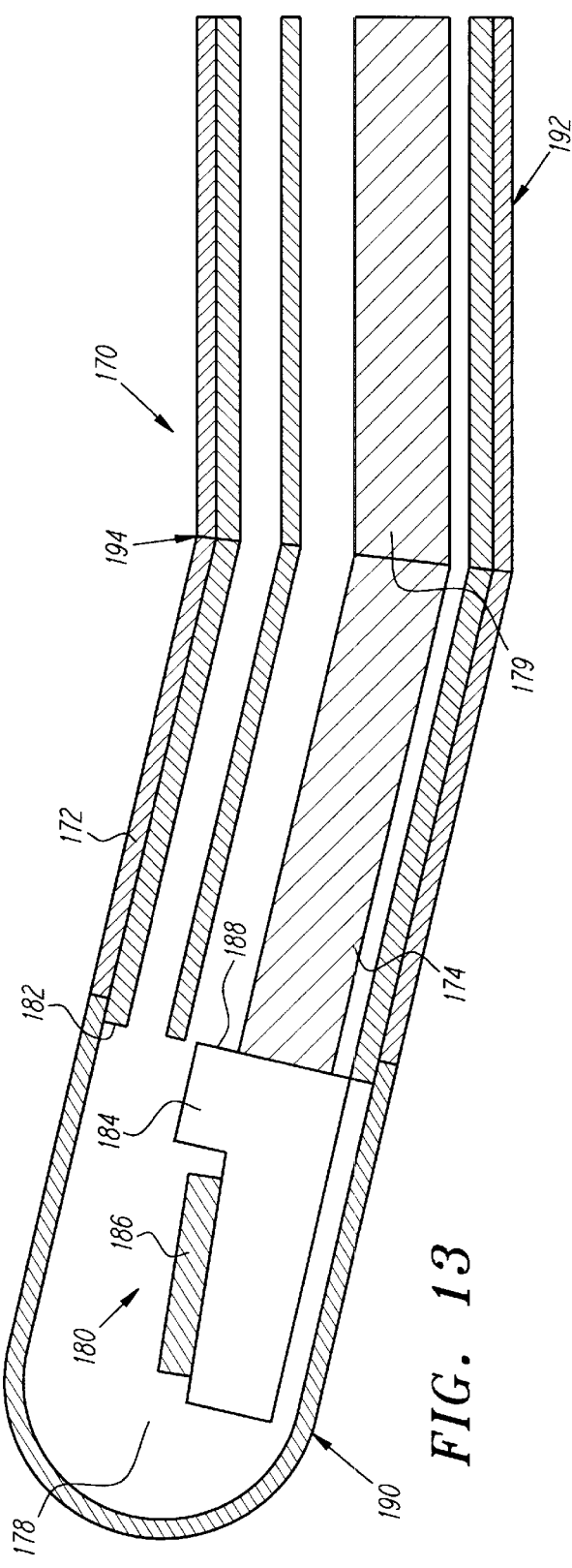

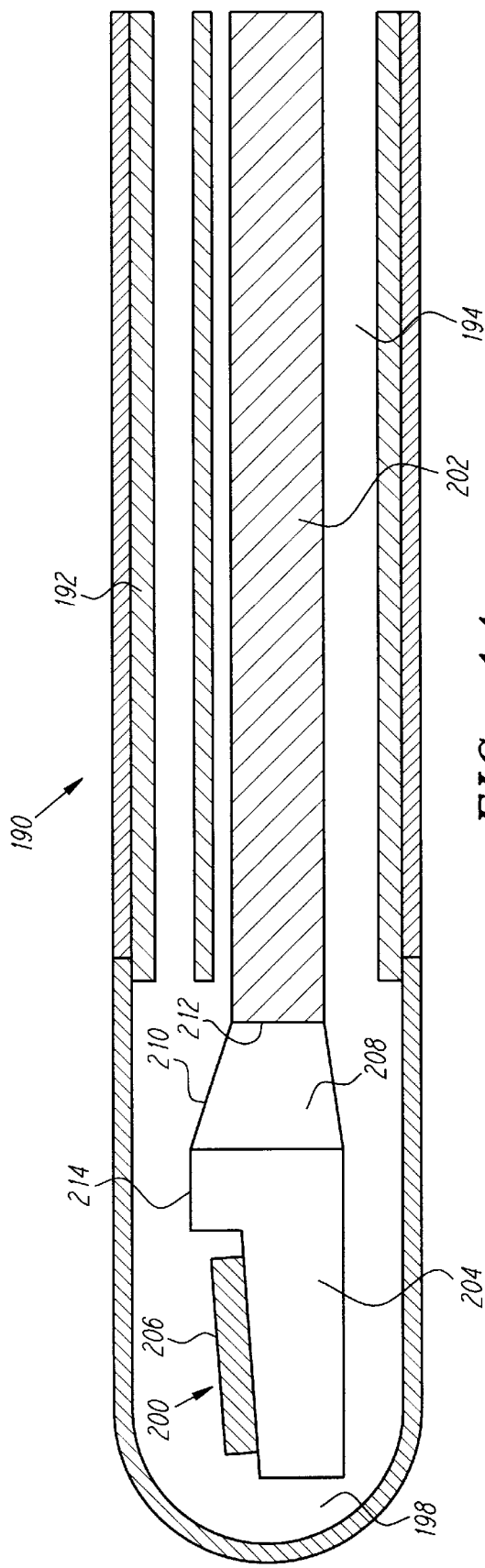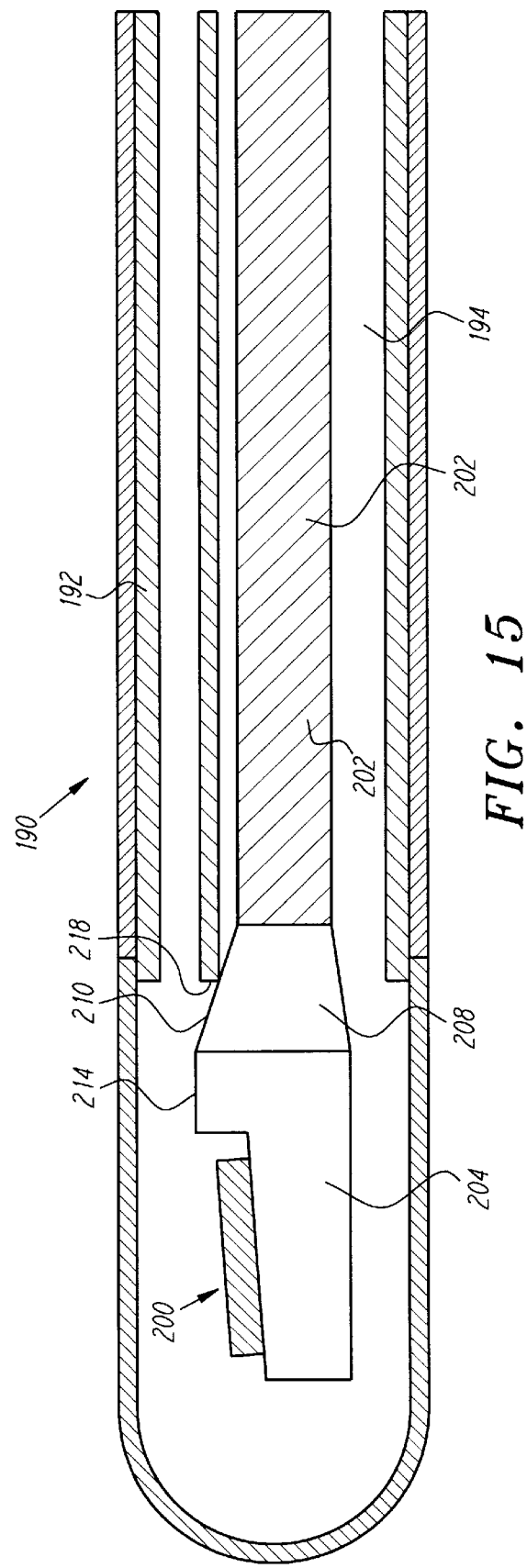

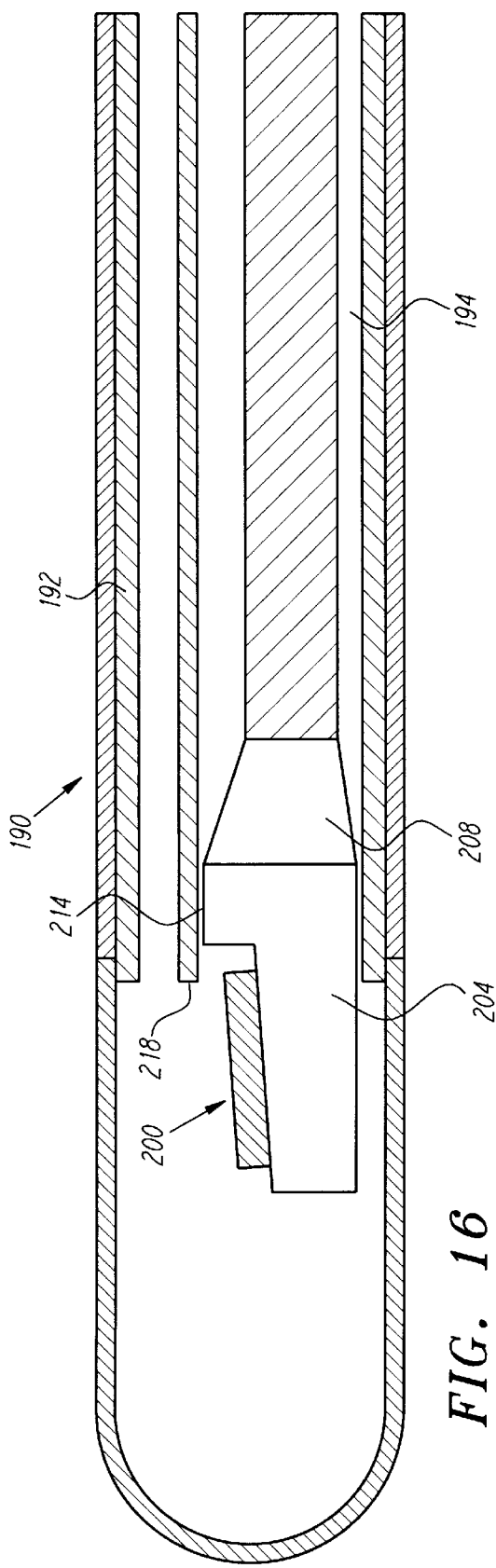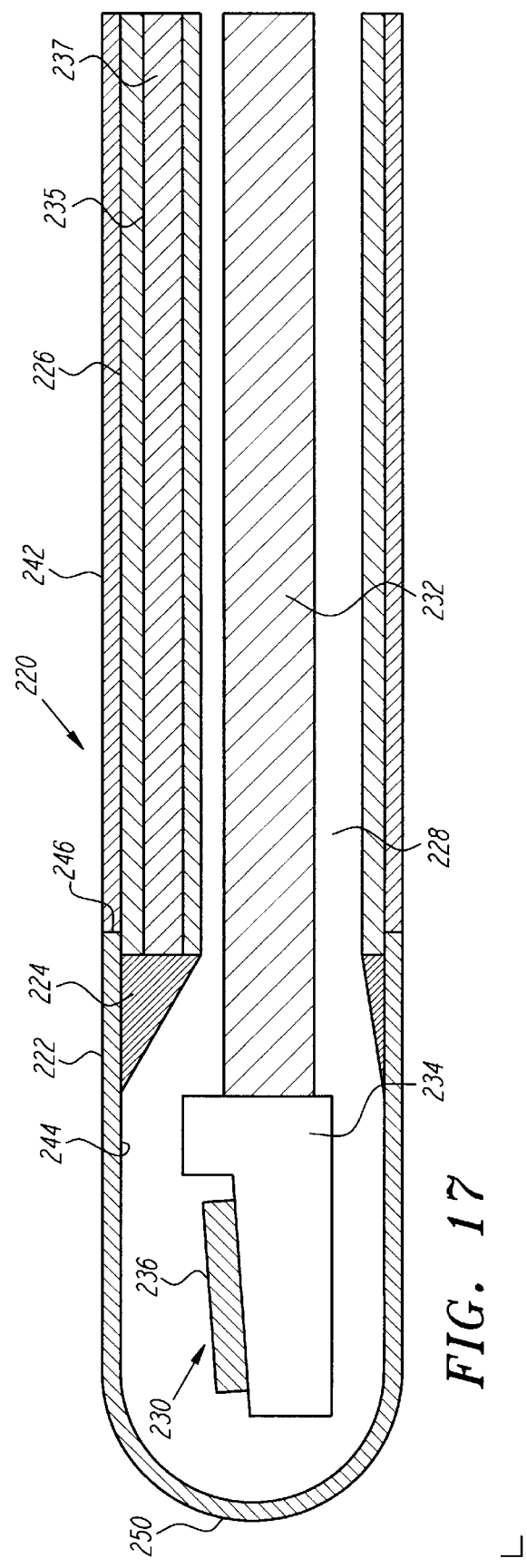

MULTIFUNCTION INTRALUMINAL ULTRASOUND CATHETER HAVING A REMOVABLE CORE WITH MAXIMIZED TRANSDUCER APERTURE

FIELD OF THE INVENTION

The present invention pertains to catheter systems and, more particularly, to intraluminal ultrasound catheter assemblies used in diagnostic and therapeutic applications.

BACKGROUND

Currently, most intraluminal ultrasound catheter assemblies employ a single transducer mounted inside a rotating housing. In particular, the transducer transmits and receives ultrasonic waves while the transducer housing rotates about a fixed axis in an acoustic imaging window located at a distal tip of the catheter. The rotational motion of the transducer housing is transmitted through a flexible drive-shaft that extends through an axially disposed lumen of the catheter, wherein the drive-shaft has one end connected to a motor drive unit located at a proximal opening of the lumen, and another end connected to the transducer housing. Once the distal end of the catheter is positioned, e.g., in a patient's vascular system, a cross-sectional image of the tissue surrounding the distal catheter tip is produced by using imaging and control circuitry that are electrically coupled to the transducer via an electrical conductor extending through the drive-shaft.

The obtainable depth of the imaging view into the patient tissue surrounding the distal catheter tip generally increases with higher transducer sensitivity and lower acoustic frequency. In addition, far field beam divergence, which deteriorates far field lateral image resolution, generally increases as the transducer "aperture,"—i.e., the active surface area of the transducer—decreases. It is therefore desirable to maximize the transducer aperture in order to enhance transducer sensitivity and maintain adequate image resolution at lower acoustic frequencies. Where particular applications require high image penetration, e.g., greater than ten centimeters for whole heart imagine maximizing the transducer aperture becomes very important. However, the size of the transducer aperture is limited to the available inner diameter of the acoustic window area of the distal catheter tip, which is itself necessarily limited due to anatomical constraints, e.g., of the human cardiovascular system. Thus, the most must be made of the limited available acoustic window space for imaging.

In known two-dimensional intraluminal ultrasound catheter assemblies that perform the sole function of imaging, the size of the transducer aperture can be maximized by simply selecting an active transducer surface diameter (i.e., where the transducer surface is generally circular) that circumscribes a circle as close as possible to the inner wall of the catheter imaging window during rotation of the transducer housing. However, in assemblies that combine one or more additional functions with imaging, such as, e.g., pull-wire steerability or angioplasty balloon therapy, maximizing the transducer aperture to the available inner window circumference can be problematic.

By way of example, a conventional multi-function intraluminal ultrasound catheter assembly 20 is illustrated in FIG. 1. The catheter assembly 20 comprises a first elongate tubular element 22, which forms an axially disposed lumen 24. An acoustic imaging window 28 is attached to a distal end of the first tubular element 22, thereby forming an enclosed tip of the catheter assembly 20. A flexible drive-shaft 26 extends through the lumen 24 and is connected at a distal end to a transducer housing 32 disposed in the acoustic imaging window 28. The transducer housing 32 has a generally cylindrical transducer 30 mounted therein, exposing a circular active surface area, or aperture. A second elongate tubular element 34 is also disposed within lumen 24, wherein the second tubular element 34 forms an additional lumen 36 used for other catheter functions—e.g., to contain one or more pullwires, or to deliver liquid to a distally disposed balloon for performing angioplasty therapy.

As best seen in FIG. 1A, in order to maximize the transducer aperture, the outer diameter of the transducer housing 32 is nearly co-extensive with the inner diameter 38 of the acoustic imaging window 28. In particular, the transducer/housing assembly circumscribes a circle (shown by dashed line 37) as the transducer housing 32 rotates about a "fixed" axis 35, such that the circle 37 is just slightly smaller in diameter than the inner diameter 38 of the acoustic imaging window 28. As a result, however, the "imaging core" 25—defined herein as the drive-shaft 26 along with the connected transducer housing 32 and mounted transducer 30—cannot be "back loaded," i.e., inserted into or retracted from the catheter assembly 20, since the transducer housing 32 has a larger cross-section than does lumen 24. This is a significant drawback, as the ability to back load an imaging core has several distinct advantages. For example, with the ability to back load, the imaging core can be separately built and later inserted into the catheter assembly for imaging. Further, after use, the imaging core can be retracted from the catheter assembly and dried, thereby extending the functional life-span of the transducer.

Since back loading is not possible in catheter assembly 20, the drive-shaft 26 must be inserted through the lumen 24 before the transducer housing 32 is attached to its distal end. Only then is the transducer 30 mounted in the transducer housing 32 and, lastly, the acoustic imaging window 28 attached to the distal end of the first tubular element 22, respectively, in order to complete the catheter assembly 20.

An alternate imaging core 45 that does allow for back loading is shown in FIG. 2, with the otherwise identical catheter assembly is designated as 20'. Like the imaging core 25 depicted in FIG. 1, the alternate imaging core 45 comprises a flexible drive-shaft 46 connected at a distal end to a transducer housing 52, which has a transducer 50 mounted therein. As best seen in FIG. 2A, in order for the imaging core 45 to be back loaded through lumen 24, the outer diameter of the transducer housing 52 is limited to a size slightly less than the remaining available diameter 57 of the lumen 24 after the outer diameter 55 of the second tubular element 34 (shown in dashed lines for purposes of illustration) is accommodated.

While this alternate configuration allows for back loading of the imaging core 45, a resultant drawback is that the available surface diameter of the transducer 50 must be much smaller than the inner diameter 38 of the acoustic window 28. As such, the imaging core 45 produces a two-dimensional cross-sectional image that is inferior to that produced by the imaging core 25 illustrated in FIG. 1.

SUMMARY OF THE INVENTION

The present invention overcomes the afore-described drawbacks of conventional intraluminal ultrasound catheter systems by providing a catheter assembly that allows for the insertion and retraction of an imaging core through a lumen having a cross-section that, through at least a portion of the lumen, has a dimension that is less than the available diameter of an acoustic imaging window located at a distal end of the catheter assembly, while still providing for a maximized transducer aperture.

In a preferred embodiment, the catheter assembly includes an elongate tubular element that forms an axially disposed lumen having at least a first portion with a flat inner wall forming a "D-shaped" cross-section. An acoustic imaging window having a circular cross-section is connected to a distal end of the elongate tubular element, thereby forming an enclosed tip of the catheter assembly. In particular, the cross-sectional dimension of the D-shaped portion of the lumen that extends from the flat inner wall is less that the available inner diameter of the imaging window. A flexible drive-shaft extends through the lumen and is connected to a transducer housing disposed in the acoustic imaging window area, the transducer housing having a transducer mounted therein, the drive-shaft, transducer housing and mounted transducer respectively comprising a preferred imaging core.

In accordance with a general aspect of the invention, the transducer housing has a substantially "D-shaped" perimeter at its greatest outer dimensions, wherein a radially arcuate portion of the transducer housing defines the circular portion, and a first longitudinally disposed cut-away portion of the transducer housing defines the flat portion, respectively, of the "D-shape." The radially arcuate portion of the transducer housing forms a partial cylindrical shape having an outer diameter that is nearly co-extensive with the inner diameter of the acoustic imaging window. The transducer housing includes a second longitudinally disposed cut-away portion forming a transducer mounting section, which is configured such that the active surface of a transducer mounted therein is generally aligned across the maximal diameter of the radially arcuate portion of the housing. In this manner, the transducer aperture can still be maximized with respect to the available inner diameter of the acoustic imaging window.

The imaging core may be retracted from the catheter assembly (and later re-inserted) by first rotating the transducer housing such that its D-shaped portion is substantially aligned with the D-shaped cross-section of the lumen. In particular, the outer perimeter of the D-shaped portion of the transducer housing is preferably slightly smaller at each corresponding dimension than the D-shaped portion of the lumen, so that the transducer housing may not be inserted or retracted therethrough unless the respective transducer housing and lumen cross-sections are similarly oriented with each other.

Other and further objects, features, aspects, and advantages of the present invention will become better understood with the following detailed description of the accompanying drawings.

BRIEF DESCRIPTION OF THE DRAWINGS

The drawings illustrate both the design and utility of preferred embodiments of the present invention, in which:

FIG. 1 is a cut-away, partial side view of a prior art multi-function intraluminal ultrasound catheter assembly;

FIG. 1A is a cross-sectional view taken along lines A—A in FIG. 1;

FIG. 3 is a cut-away, partial side view of a first preferred multi-function intraluminal ultrasound catheter assembly in accordance with the present invention, including a partially retracted imaging core;

FIG. 3A is a cross-sectional view taken along lines A—A in FIG. 3;

FIG. 4 is a cut-away, partial side view of the preferred catheter assembly of FIG. 3, wherein the imaging core is fully inserted;

FIG. 4A is a cross-sectional view taken along lines A—A in FIG. 4;

FIGS. 8–11 are cut-away, partial side views of a still further preferred multi-function catheter assembly, illustrating insertion of a preferred imaging core;

FIG. 8A, 9A, 10A, and 11A are cross-sectional views taken along lines A—A in FIGS. 8, 9, 10 and 11, respectively;

FIGS. 12–13 are cut-away, partial side views of a still further preferred multi-function catheter assembly, illustrating a three point bending procedure employed to facilitate retraction of a preferred imaging core;

FIG. 14 is a cut-away, partial side view of a still further preferred multi-function intraluminal ultrasound catheter assembly, including a preferred transducer housing having a tapered body section;

FIGS. 15–16 are cut-away, partial side views of the catheter assembly of FIG. 14, illustrating the retraction of its preferred imaging core;

FIG. 17 is a cut-away, partial side view of a still further preferred multi-function intraluminal ultrasound catheter assembly, including a sloped transition section at the proximal opening of its acoustic imaging window.

DETAILED DESCRIPTION OF THE PREFERRED EMBODIMENTS

Figure 2:
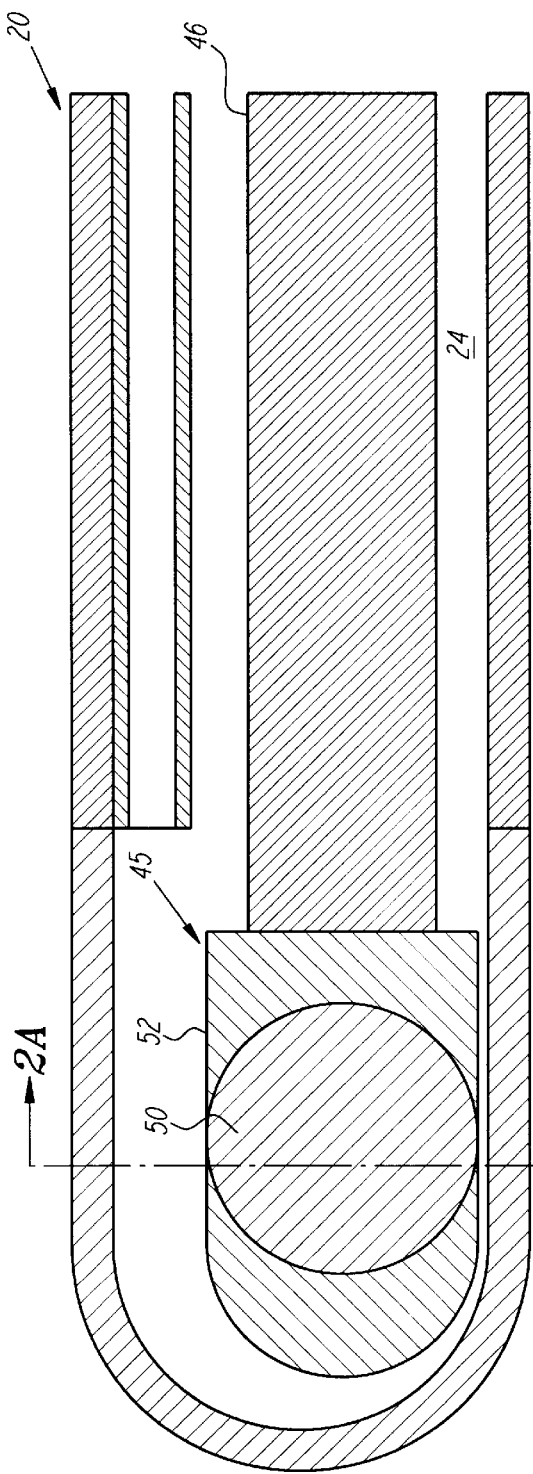
FIG. 2 is a cut-away, partial side view of the catheter assembly of FIG. 1, employing an alternate imaging core.
Figure 2A:
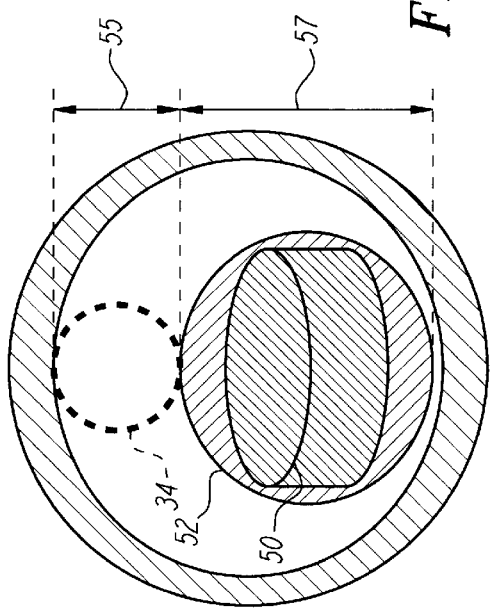
FIG. 2A is a cross-sectional view taken along lines A—A in FIG. 2.

Referring to FIG. 3, a preferred multi-function intraluminal ultrasound catheter assembly 100 includes an elongate tubular element 102, which forms a first axially disposed lumen 104 having a substantially "D-shaped" cross-section (best seen in FIG. 3A). In particular, the inner dimensions of the D-shaped lumen 104 are sufficient to allow a preferred imaging core 118 to be removably disposed therein. The imaging core 118 includes a flexible drive-shaft 120 connected to a transducer housing 122 having a generally cylindrical transducer 124 mounted therein. A "solid" portion 106 of the elongate tubular element 102 (also best seen in FIG. 3A) forms a smaller, substantially circular lumen 108, which is used for supporting other functions, such as, by way of non-limiting examples, pull wire steerability, drug delivery, balloon angioplasty, laser ablation, or for housing a stiffening member to help prevent the collapsing of the catheter assembly 100.

A cover tube 110 formed of a suitable material, such as a heat shrinkable nylon, urethane, polyethylene or other plastic, is snugly disposed around the tubular element 102, wherein the cover tube 110 provides both structural integrity to the catheter assembly 100, as well as a smooth outer surface for ease in axial movement through a patient's body passage, e.g., the vascular system, with minimal friction. A dome-shaped acoustic window 112 having its proximal end open and its distal end rounded is attached to a distal outer circumferential portion of the tubular element 102 to form an enclosed catheter tip 114, with respective ends of the cover tube 110 and acoustic window 112 bonded together at a common joint 116. As will be apparent to those skilled in the art, the outer diameter of the proximal end of window 112 is preferably substantially equal to that of the installed cover tube 110, so that a smooth outer surface is provided at joint 116.

In accordance with a first general aspect of the invention, the transducer housing 122 has an arcuate "D-shaped" perimeter at its greatest outer dimensions, i.e., at its proximal end 111, wherein the D-shaped cross-section of the transducer housing 122 is slightly smaller at each corresponding dimension than the D-shaped lumen 104 (best seen in FIG. 3A). As such, the imaging core 118 may be inserted or retracted from the catheter assembly 100 by first rotating the transducer housing 122 so that its D-shaped perimeter is substantially similarly oriented with the inner, D-shaped cross-section of lumen 104.

In accordance with a further general aspect of the invention, the transducer housing 122 has a longitudinally disposed cut-away portion 113, which slopes at a slight angle α with respect to a center axis of the drive-shaft 120 (shown as dashed-line 126) from a distal end 117 of the housing 122 toward its proximal end 111. The transducer 124 is mounted in the cutaway portion 113 of the transducer housing 122 ,such that its active surface 119 also slopes at an angle α with respect to the center axis 126 of the drive-shaft 120, and extends substantially across the inner diameter of the acoustic window 112.

In a presently preferred embodiment, the drive-shaft 120 is attached to the distal end 111 of the transducer housing 122 such that the center axis 126 of the drive-shaft 120 is substantially aligned with the axial center of mass of the transducer housing 122 (and mounted transducer 124). As is known to those skilled in the art, when freely rotating, the imaging core 118 will tend to spin about its center of gravity. In particular, the flexible drive-shaft 120 is an element with rotational symmetry. Therefore the centerline 126 of the drive-shaft 120 is also the line around which the cross-section has the smallest moment of inertia. Thus, rotation of the drive-shaft 120 should take place around this center axis 126 to prevent vibrations and additional rubbing/friction of the drive-shaft 120 against the wall 107 of lumen 104.

On the other hand, the transducer housing 122 with the mounted transducer 124 is not a rotation-symmetrical element. Thus, the center axis 126 of the drive-shaft 120 should be aligned to pass through the center of gravity of the transducer housing 120 and mounted transducer 124, so that the axis of rotation remains that which has the smallest moment of inertia. This way no centripetal force is necessary to keep the transducer housing 120 rotating. Otherwise, the transducer housing 120 and transducer 124 will bend away from the axis of rotation until interaction with the inner surface 115 of the imaging window 112 provides this centripetal force. The reaction of this force is a centrifugal force applied by the transducer housing 120 and/or transducer 124 to the inner wall 115 of the acoustic window 112, causing undesirable vibrations, friction and wear.

In particular, while rotating, the circumscribed circle of the transducer housing 120 should preferably fit within the inner contour of the imaging window 112. When the imaging core 118 is passed through the D-shaped lumen 104 and the transducer housing 120 and transducer 124 extends into the imaging window 112, its position is typically eccentric. As such, at the onset of rotation, the circumscribed circle of the transducer housing 120 and transducer 124 does not fit within the inner contour of the imaging window 112, because of this eccentric position. However, interaction forces between the inner wall 115 of the imaging window 112 and the transducer housing/transducer 120/124 will force the distal portion of the imaging core 118 to better align with the center axis of the catheter assembly 100 (shown as dashed line 127), so that the circumscribed circle of the transducer housing/transducer 120/124 will fit within the inner contour of the imaging window 112—i.e., the centerline of the drive-shaft 126 will match up with the centerline 127 of the catheter assembly 100.

By way of illustration, as seen in FIG. 4, once the transducer housing 122 is positioned within the imaging window 112 and is rotated, the resulting interaction between the rotating transducer housing 122 and inner surface 115 of the acoustic window 112 will cause the center axis 126 of drive-shaft 120 to re-position itself to be aligned with the center axis 127 of the distal section of the catheter assembly 100. As best seen in FIG. 4A, once the respective drive-shaft axis 126 and catheter assembly axis 127 are aligned, the transducer housing 120 properly sized, respectively, such that a circle 128 circumscribed by the portion of the transducer housing 122 furthest from the center axis 126/127 (i.e., at a radius r) does not intersect the inner wall 115 of the acoustic imaging window 112 as the housing 122 freely rotates, thereby avoiding unwanted oscillation of the transducer housing 122 and resulting damage to the inner wall 115 of the acoustic imaging window 112. Further, in order to minimize the bending stress of the drive-shaft 120 at its connection to the proximal end of the transducer housing 122, the diameter of the drive-shaft 120 is preferably small enough to allow its center axis 126 to coincide with the axis 127 of the catheter assembly 100, without contacting the inside wall 107 of tubular element 102 during rotation.

As will be apparent from the present disclosure to those skilled in the art, the tubular element 102 can be extruded from a suitable material in a number of ways. By way of non-limiting examples, the tubular element 102, including the solid portion 106, can be extruded from a single die. Alternatively, the solid portion 106 can be extruded as a separate piece having the circular lumen 108 disposed therethrough, wherein the solid portion 106 is then suitably bonded to the inside wall of the tubular element 102, i.e., in the otherwise substantially circular lumen 104, in order to form the "D-shape". Further, with the benefit of the present disclosure, it will also be apparent to those skilled in the art that the respective cross-section of the lumen 104 and outer perimeter the transducer housing 122 need not necessarily be "D-shaped" in order to achieve the afore-described advantage of the present invention, but can alternately be formed in any of a number of non-rounded shapes, so long as the selected lumen provides for passage of a selected matching-shaped transducer housing in at least a first rotational orientation, and so long as the selected transducer housing accommodates a transducer which has at least one—i.e., "width-wise"—dimension that substantially spans the available inner diameter of the acoustic imaging window portion of the catheter assembly.

Figure 5B:
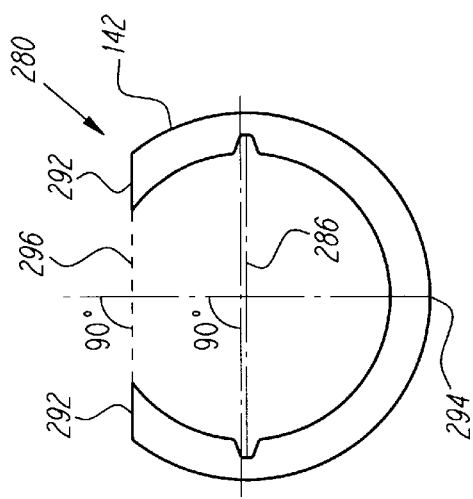
FIG. 5B is a front end view of the transducer housing of FIG. 5A.
Figure 5C:
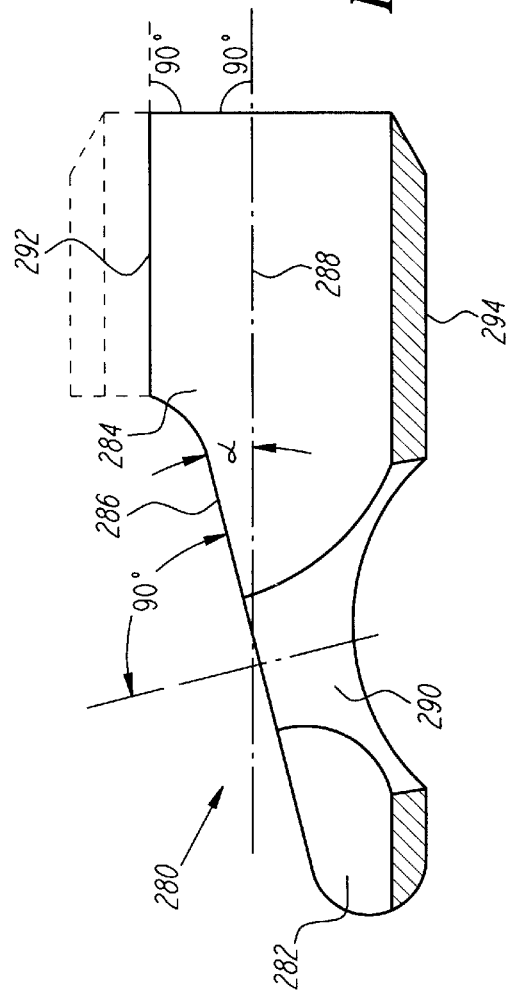
FIG. 5C is a partial cut-away elevation of the transducer housing of FIG. 5A.
Figure 5A:
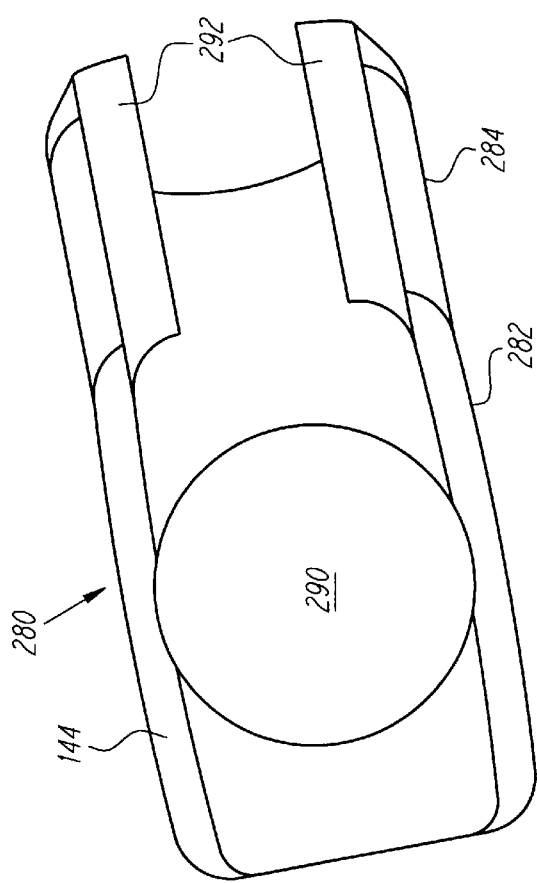
FIG. 5A is a perspective view of a first preferred transducer housing, in accordance with a more particular aspect of the present invention.

Referring to FIGS. 5A–C, a first preferred embodiment of a transducer housing 280 will now be described in detail. Housing 280 has a generally cylindrical shape, and comprises transducer and drive-shaft mounting sections 282 and 284, respectively. In particular, by using techniques known in the art, the distal portion of the transducer housing 280 is "cut away", thereby forming the transducer mounting section 282 having a mounting plane 286 at an angle α relative to a center axis 288 of the "pre-cut" housing 280 (best seen in FIG. 5C). A transducer mounting hole 290 is then formed, e.g., by drilling through the transducer mounting section 282 of the housing 280, in a direction substantially perpendicular to the mounting plane 286. The transducer is mounted through the transducer mounting hole 290 of the transducer housing 280, wherein the edge of the transducer makes contact with the edge of hole 290.

The drive-shaft mounting section 284 is formed by cutting off the top proximal portion of housing 280, so that the resulting edges 292 of the mounting section 284 are substantially parallel to the "bottom" 294 of the housing 280. In presently preferred embodiments, the angle α between the transducer mounting plane 286 and the axis of the "pre-cut" housing 280 is between 5 and 15 degrees. Because a transducer (not shown) mounted in transducer mounting hole 290 will be tilted at an angle, the resulting ultrasonic signal will sweep in a conical, rather than a circular pattern when rotated by a drive-shaft (not shown) mounted in the drive-shaft mounting section 284 of the housing 280. In this manner, the transducer does not directly receive undesirable acoustic signals reflecting off of the inner wall of an acoustic window in which the transducer housing 280 is spinning.

In accordance with known practice, the area surrounding the drive-shaft within the drive-shaft mounting section 284 of the transducer housing 280 the transducer housing is filled with a potting material (not shown), which is leveled off flush with the cut-away edges 292, forming a substantially flat surface 296 therebetween. In this manner, the drive-shaft mounting section 284, which forms the largest outer perimeter of the transducer housing 280, is "D-shaped" (best seen in FIG. 5B).

Figure 6B:
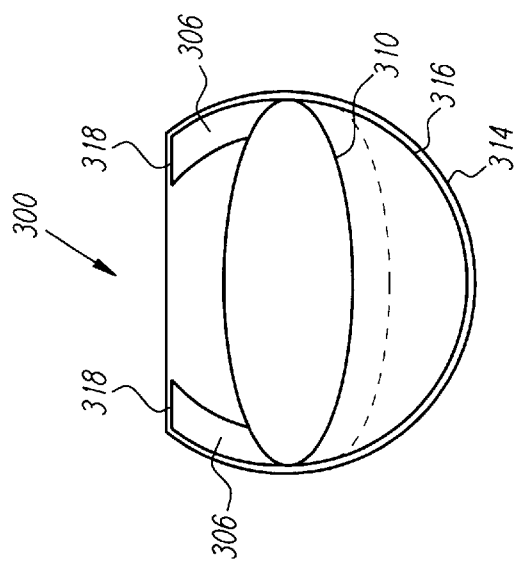
FIG. 6B is a front end view of the transducer housing of FIG. 6A.
Figure 6A:
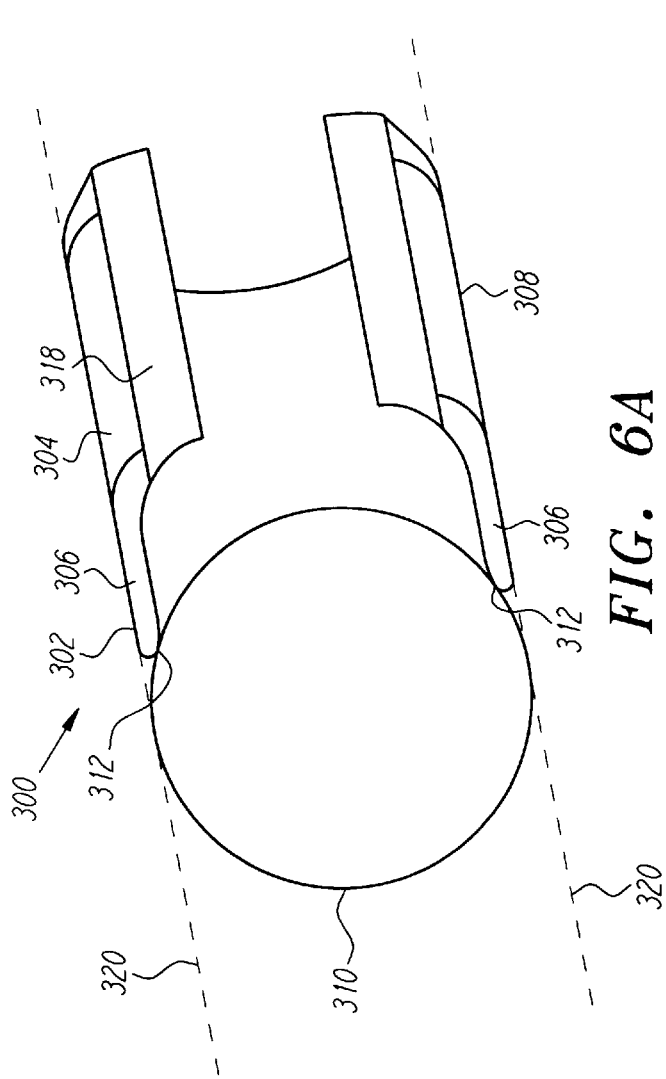
FIG. 6A is a perspective view of a second preferred transducer housing, in accordance with a further more particular aspect of the present invention.
Figure 6C:
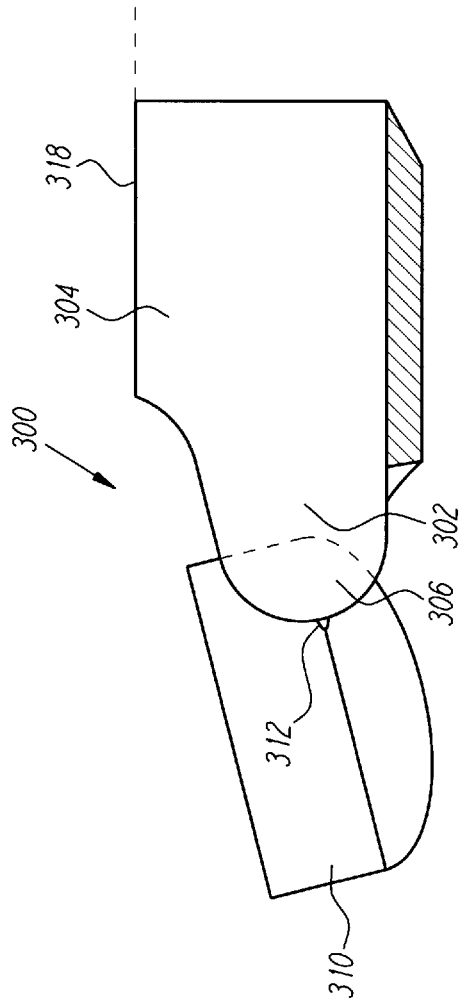
FIG. 6C is a partial cut-away elevation of the transducer housing of FIG. 6A.

Referring to FIGS. 6A–C, an alternate preferred embodiment of a transducer housing 300 has a "fork-shaped" transducer mounting section 302, wherein the top proximal portion of housing 300 is cut-away to form a pair of edges 318 of a drive-shaft mounting section 304. The distal portion of housing 300 is cut-away to form the transducer mounting section 302 having a pair of opposing arms 306 that are spread far enough apart to effectively grasp a "cup-shaped" transducer 310, which is attached to the inside surface of the arms 306 by suitable means, such as adhesive bonding. As will be apparent to those skilled in the art, the transducer housing 300 described with reference to FIGS. 6A–C provides for a greater transducer aperture, since the outer circumferential edge of the transducer 310 extends fully to the outer edges of housing 300, as represented by dashed lines 320 in FIG. 6A—i.e., the walls of housing 300 do not occupy any space that can be used to maximize the transducer 310. As will be further apparent to those skilled in the art, this fork-shaped transducer housing design may also be advantageously employed in a conventional imaging catheter assembly (e.g., such as in assembly 20 of FIG. 1).

In presently preferred embodiments, each of the tips of arms 306 comprises a tooth 312 on the inside surface, so that the transducer 300 can more easily be grasped and fixed during the application and curing of the bonding material. Because the edges of the transducer 310 are exposed, thus making it possible for the outer edge of transducer 310 to make contact with the inner wall of an elongate tubular element 314, the bottom of transducer 310 must be rounded off at an arc equal to that of a D-shaped lumen 316 formed by tubular element 314, as best seen in FIG. 6B, so that the aperture of the transducer 310 can be fully maximized.

Figure 7:
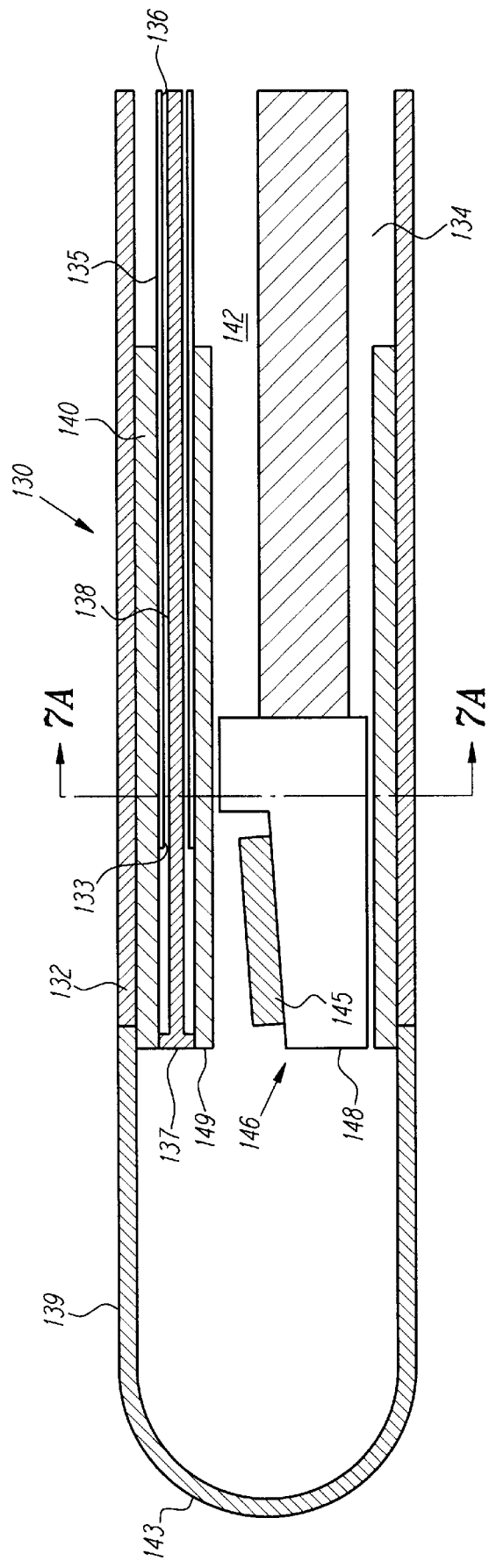
FIG. 7 is a cut-away, partial side view of a further preferred multi-function intraluminal ultrasound catheter assembly, including a partially retracted imaging core.

Referring to FIG. 7, an alternate preferred multi-function intraluminal ultrasonic catheter assembly 130 includes a first elongate tubular element 132, which forms a substantially circular lumen 134. For purposes of simplification, the tubular element 132 is assumed to incorporate and embody the same properties of both a "cover tube" and of a flexible but supportive body element for forming and protecting lumen 134. A second elongate tubular element 135 having a substantially smaller outer diameter than tubular element 132 extends through lumen 134 in an off-center position, adjacent the inner wall of tubular element 132. The second tubular element 135 forms a substantially circular lumen 136 having a steering pullwire 138 disposed therein. A dome-shaped acoustic window 139 having its proximal end open and its distal end rounded is attached to a distal outer circumferential portion of the tubular element 132 to thereby form an enclosed catheter tip 143.

Figure 7A:
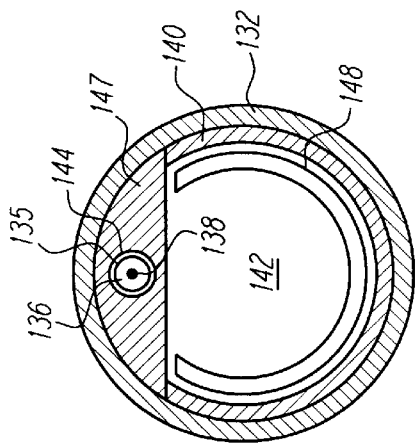
FIG. 7A is a cross-sectional view taken along lines A—A in FIG. 7.

A third tubular element 140 is disposed within lumen 134 at a distal end of the first tubular element 132, wherein the third tubular element 140 forms a substantially D-shaped lumen 142 (best seen in FIG. 7A). In accordance with a general aspect of the present invention, the D-shaped lumen 142 is sized to accommodate a retractable imaging core 146 comprising a substantially D-shaped transducer housing 148 (also best seen in FIG. 7A) having a cylindrical transducer 145 mounted therein. A solid portion 147 of the third tubular element 140 forms a substantially circular lumen 144 having a slightly larger diameter than the outer diameter of the second tubular element 135. In this manner, the second tubular element 135 may be accommodated partially through lumen 144, wherein the steering pullwire 138 extends through a distal opening 133 of the second tubular element 135 and is anchored at a distal end 137 of the third tubular element 140.

As will be appreciated by those skilled in the art, the third tubular element 140 is preferably composed of a flexible material, such as a low density polyethylene or EVA, which provides sufficient flexibility to allow the tubular element 140 to bend during steering maneuvers—i.e., when pullwire 138 is "pulled." In this manner, the third tubular element 140 contributes to the steering mechanism of the catheter assembly 130, while still providing a lumen 142 of sufficient dimension to allow the transducer housing 148 to pass therethrough when rotated to a substantially similar orientation.

For purposes of further illustration and clarification, FIGS. 8–11 illustrate the insertion of a simplified preferred imaging core 160 comprising a transducer housing 164 connected to a drive-shaft 162 into a still further preferred intraluminal ultrasound catheter assembly 150. The catheter assembly 150 includes an internally disposed tubular element 152, which forms a first axially disposed lumen 154 having a substantially D-shaped cross-section. The tubular element also forms a second, substantially circular lumen 153 disposed in an otherwise solid portion 155, wherein the second lumen 153 is used to support further catheter functionality, such as, e.g. pull-wire steerability, laser ablation, angioplasty balloon therapy, etc. The catheter assembly 150 includes an acoustic imaging window 156 having a substantially circular cross-section at its distal end, forming an enclosed tip of the catheter assembly.

As depicted in FIGS. 8-8A and 9-9A, the D-shaped outer perimeter of the transducer housing 164 must be rotationally and specifically oriented with the D-shaped lumen 154 in order to pass through lumen 154 into an imaging area 158 located within the acoustic imaging window 156. In particular, FIG. 8 depicts the transducer housing 164 rotationally disoriented with respect to lumen 154—i.e., such that the transducer housing 164 (shown in phantom in FIG. 8A) cannot be inserted into the lumen 154. FIG. 9 depicts the insertion of the transducer housing 164 into lumen 154 after the D-shaped perimeter of the transducer housing 164 has been specifically and rotationally oriented with the D-shaped lumen 154 (best seen in FIG. 9A).

As illustrated in FIGS. 10 and 11, once the outer perimeter of the transducer housing 164 is specifically and rotationally oriented with the D-shaped cross-section of lumen 154, the transducer housing 164 may be pushed through lumen 154 into the imaging area 158, wherein the center axis 166 of the imaging core 160 is moved into alignment with the center axis 167 of the catheter assembly 150 when the drive-shaft 162 is rotated.

In particular, if the center axis 166 of the imaging core 160 was not aligned with the center axis 167 of the catheter assembly 150 during rotation, a circumscribed circle 168, representing the portion of the transducer housing 164 (shown in phantom in FIG. 10A) extending furthest from the drive-shaft axis 166 would intersect the inner wall 157 of window 156, thereby causing oscillation of the housing 164 and damage to the acoustic window 156, respectively. FIG. 11 illustrates the position of the transducer housing 164 once the imaging core 160 is properly aligned, so that circumscribed circle 168 does not intersect the inner wall 157 of window 158, thereby avoiding oscillation of the transducer housing 164 and damage to window 156.

Referring to FIGS. 12–13, a "three-point bending in the proper plane procedure" is demonstrated with respect to a still further preferred multi-function intraluminal ultrasound catheter assembly 170 designed in accordance with the present invention, wherein an imaging core 180 comprising a drive-shaft 179, transducer housing 184, and a mounted transducer 186, respectively, is axially displaced through a D-shaped lumen 174 formed by elongate tubular element 172.

As can be observed in FIG. 12, merely pulling the proximal end of the drive-shaft 179 will cause the proximal end 188 of the transducer housing 184 to butt up against the distal end 182 of tubular element 172, thereby preventing the transducer housing 184 from being retracted out of the acoustic window area 178 of the catheter assembly 170 and into lumen 174. Instead, as depicted in FIG. 13, the transducer housing 184 must first be specifically aligned and rotationally oriented, as well as axially aligned, with lumen 174, before the imaging core 180 can be retracted from the acoustic window area 178.

This may be accomplished by manipulating the catheter assembly 170 so that the tubular element 172 undergoes a three-point bending in the proper plane (also depicted in FIG. 13). In particular, by simultaneously applying a force at points 190, 192 and 194, the distal end 182 of tubular element 172 is displaced, with the transducer housing 184 becoming axially aligned with lumen 174. The drive-shaft 179 is then rotated until the D-shaped perimeter of the transducer housing 184 is specifically and rotationally oriented with the D-shaped cross-section of lumen 174. The imaging core 180 can then be retracted from the catheter assembly 170 (i.e., by pulling the proximal end of the drive-shaft 179).

Referring to FIG. 14, a further exemplary multi-function intraluminal ultrasound catheter assembly 190 includes an elongate tubular element 192, which forms a substantially D-shaped lumen 194, i.e., in a manner essentially the same as the afore-described preferred imaging catheter assembly 100. The catheter assembly 190 further includes an alternate preferred imaging core 200 comprising a drive-shaft 202 attached to a D-shaped transducer housing 204 having a transducer 206 mounted therein, wherein the transducer housing 204 includes a tapered section 208 at its proximal end. In particular, the tapered section 208 has a sloped, flat edge 210 that extends from a middle portion 214 of the transducer housing 204 to the proximal end 212, wherein the circumference of housing 204 at its proximal end 212 is substantially equal to the diameter of the attached drive-shaft 202. In other words, the outer perimeter of portion 208 of the transducer housing 204 maintains a D-shape as it tapers down to the proximal end 212, i.e., with the sloped edge having a triangular shape as it tapers to end 212.

As will be appreciated by those skilled in the art, the tapered section 208 of the transducer housing 204 allows the imaging core 200 to be easily retracted out of an acoustic window area 198 of the catheter assembly and through lumen 194, i.e., without requiring a "three-point bending" procedure. As such, an advantage of this alternate preferred configuration of the transducer housing 204 is that it is thereby possible to exchange preferred imaging cores constructed in accordance with the principles of the present invention without removing the catheter assembly 190 from a patient's body.

In particular, as illustrated in FIGS. 15–16, to retract the transducer housing 204 into D-shaped lumen 194, the transducer housing 204 must first be rotationally oriented, so that the tapered edge 210 makes contact with the distal edge 218 of the tubular element 192 that forms the "straight edge" to the D-shape of lumen 1941. As the transducer housing 204 is retracted into the lumen 194, the tapered edge 210 slidingly engages edge 218 of tubular element 192 (seen in FIG. 15), thereby allowing the transducer housing 204 to maintain the proper rotational orientation with respect to lumen 194. Once the transducer housing 204 is safely fully retracted into lumen 194 (seen in FIG. 16), the imaging core 200 can then be quickly removed from the catheter assembly 190.

Referring to FIG. 17, a still further exemplary multifunction intraluminal ultrasound catheter assembly 220 includes an alternate preferred acoustic window portion 222 having a slowed transition section 224 at its proximal end, thereby allowing a preferred imaging core 230 constructed in accordance with the principles of the present invention to be easily retracted. More particularly, the catheter assembly 220 includes an elongate tubular element 226, which forms a first axially disposed lumen 228 having a substantially D-shaped cross-section, wherein the D-shaped lumen 228 has a sufficient cross-sectional area to allow a preferred imaging core 230 to be removably disposed therein, the imaging core 230 including a flexible drive-shaft 232 connected to a transducer housing 234 having a generally cylindrical transducer 236 mounted therein. As in the previously described preferred embodiments, the elongate tubular element 226 also forms a smaller, substantially circular lumen 235. A stiffening member 237 is disposed within the second lumen 235 to provide greater structural integrity to the catheter assembly 220. As will be apparent to those skilled in the art, the second lumen 235 may also be used for supporting other functions, such as, by way of non-limiting examples, pull wire steerability, drug delivery, balloon angioplasty, laser ablation.

A cover tube 242 formed of a suitable material, such as a heat shrinkable nylon, urethane, polyethylene or other plastic, is snugly disposed around the tubular element 226, wherein the cover tube 242 provides both structural integrity and a smooth outer surface to the catheter assembly 220. A dome-shaped acoustic window 222 having its proximal end open and its distal end rounded is attached to a distal outer circumferential portion of the tubular element 226 to form an enclosed catheter tip 250, with respective ends of the cover tube 242 and acoustic window 222 bonded together at a common joint 246.

The sloped transition section 224 has a substantially circular cross-section at its distal extremity, i.e., matching that of the portion of the inner wall 244 of the acoustic window 222, and a substantially D-shaped cross-section at its proximal extremity, i.e., matching that of the D-shaped lumen 228. The transition section 224 is formed integrally (i.e., from a single mold) with the acoustic window 222, or can be molded separately and then suitably bonded thereto. As will be appreciated, the transition section 224 allows retraction of the imaging core 230 from the catheter assembly 220 without requiring a "three-point bending" procedure, which, as described above with reference to catheter assembly 190, not only makes it easier to extract the imaging core 230 from the catheter assembly 220, but also makes it possible to exchange imaging cores without removing the catheter assembly 220 from a patient's body. In particular, the sloped section 224 acts to align the transducer housing 234 with the D-shaped lumen 228 as the imaging core 230 is retracted from the catheter assembly.

Figure 18:
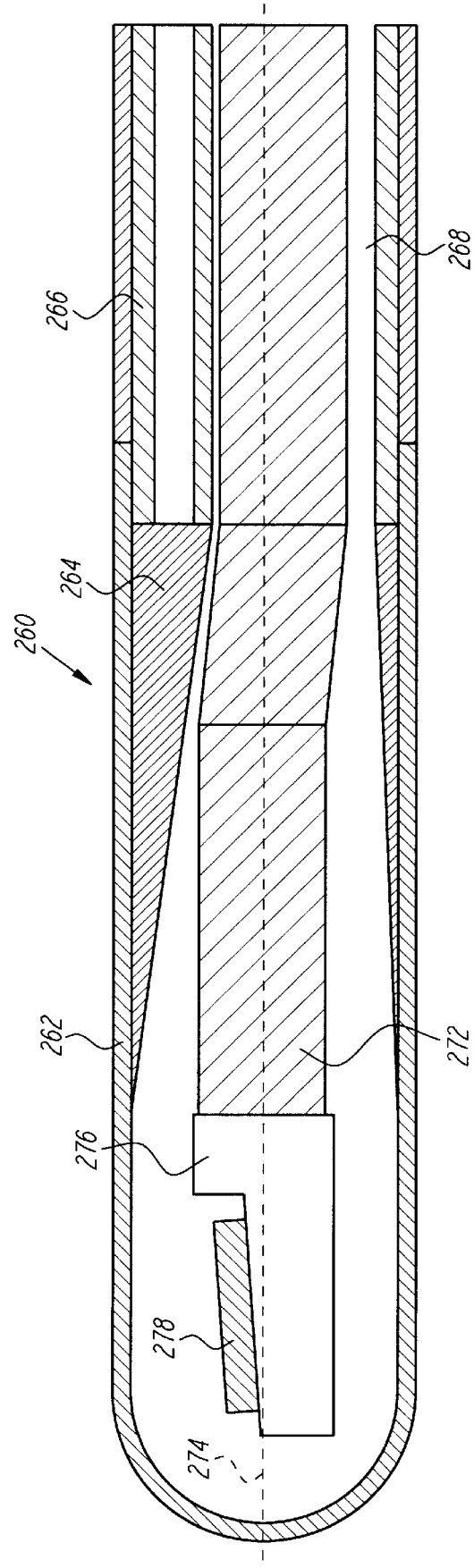
FIG. 18 is a cut-away, partial side view of a still further preferred multi-function intraluminal ultrasound catheter assembly, including an alternate sloped transition section at the proximal opening of its acoustic imaging window that allows an oversized flexible drive-shaft to align itself with the center axis of the catheter assembly.

A still further preferred multi-function intraluminal ultrasound catheter assembly 260 is shown in FIG. 18, which also includes an acoustic window portion 262 having a sloped transition section 264. In particular, the transition section 264 has a length sufficient to allow the axis of an oversized drive-shaft 272 (i.e., the diameter of drive-shaft 272 has a size wherein the inner wall of a first tubular element 266 forming a D-shaped lumen 268 hinders the drive-shaft 272) to self-compensate for any axis misalignment between the drive-shaft 272 and the center axis 274 of the catheter assembly 260. In this manner, the drive-shaft 272 can bend within transition section 264 so that the rotational center of gravity of the transducer housing 276 and mounted transducer 278 can re-align with the center axis 274 in the imaging window area 262, when the transducer housing 276 is rotating.

As will be apparent from the present disclosure to those skilled in the art, the inner sloped sections 224 and 264 of the afore-described alternate preferred catheter assemblies 220 and 260, respectively, may in still further preferred embodiments be placed in a more proximal location within a catheter assembly—i.e., and not as part of the acoustic window portion.

While embodiments and applications of this invention have been shown and described, as would be apparent to those skilled in the art, many more modifications and applications are possible without departing from the inventive concepts herein.

By way of example only, the afore-described inventive techniques for providing an imaging core with a transducer housing having reduced dimensions, while still capable of seating a transducer with a maximized aperture with respect to the acoustic window diameter, has been described in context of multi-lumen catheter assemblies. However, the advantages gained by that aspect of the present invention may be equally applicable in single lumen catheters. By way of another example, while the afore-described preferred embodiments are directed only to double lumen assemblies, it will be readily apparent to those skilled in the art that the advantages gained by the present invention will be equally applicable if still further lumens are provided. By way of a still further example, while the foregoing preferred embodiments are directed to closed-end catheter assemblies, the advantages of the invention are equally gained in an open-ended assembly.

The scope of the disclosed inventions, therefore, is not to be restricted except in the spirit of the appended claims.

What is claimed:

1. An ultrasonic imaging catheter assembly, comprising:
    an elongate tubular element having a lumen having a first portion with a non-circular, generally D-shaped cross-section; and
    a rotatable imaging core comprising a drive-shaft attached to a transducer housing, the transducer housing having at its greatest dimension a non-circular outer perimeter substantially similar in dimension to the non-circular, generally D-shaped cross section of the first lumen portion, wherein the imaging core may be passed through the lumen if the outer perimeter of the transducer housing and cross-section of the first lumen are similarly oriented.

2. The ultrasonic imaging catheter assembly of claim 1, further comprising a generally cylindrical imaging window, the lumen accessing the imaging window, wherein the transducer housing is configured to mount a transducer having a generally circular surface in a manner such that a diameter of the transducer surface substantially spans an inner diameter of the imaging window.

3. The ultrasonic imaging catheter assembly of claim 2, further comprising a transducer having a generally circular surface mounted in a longitudinal cut-away portion of the transducer housing, wherein a circle circumscribed by a circumferential edge of the transducer surface as the imaging core is rotated has a diameter nearly co-extensive with the inner diameter of the imaging window.

4. The ultrasonic imaging catheter assembly of claim 1, the transducer housing having a tapered body portion proximate the drive-shaft configured to align the outer perimeter of the transducer housing with the first lumen potion cross-section as the imaging core is retracted from the catheter assembly.

5. The ultrasonic imaging catheter assembly of claim 1, further comprising a sloped body portion configured to align the outer perimeter of the transducer housing with the first lumen portion cross-section as the imaging core is retracted from the catheter assembly.

6. The ultrasonic imaging catheter assembly of claim 1, the elongate tubular element forming a second lumen.

7. The ultrasonic imaging catheter assembly of claim 6, wherein the second lumen is adapted to house a steering pullwire.

8. A ultrasonic imaging catheter assembly, comprising:

an elongate tubular element forming first and second lumens, the first lumen having at least one portion with a substantially D-shaped cross-section; and a rotatable imaging core comprising a drive-shaft attached to a transducer housing, the transducer housing having at its greatest dimension a substantially D-shaped outer perimeter similar in dimension to the D-shaped cross-section of the first lumen portion, wherein the imaging core may be passed through the first lumen only if the D-shaped outer perimeter of the transducer housing and D-shaped cross-section of the first lumen portion are similarly oriented.

9. The ultrasonic imaging catheter assembly of claim 8, further comprising:

a generally cylindrical imaging window, the first lumen accessing the imaging window; and a transducer having a generally circular surface mounted in a longitudinal cut-away portion of the transducer housing, wherein a circle circumscribed by a circumferential edge of the transducer surface as the imaging core is rotated has a diameter nearly co-extensive with an inner diameter of the imaging window.

10. The ultrasonic imaging catheter assembly of claim 8, the transducer housing having a tapered body portion proximate the drive-shaft configured to align the D-shaped outer perimeter of the transducer housing with the D-shaped cross-section portion of the first lumen as the imaging core is retracted from the catheter assembly.

11. The ultrasonic imaging catheter assembly of claim 8, further comprising a sloped body portion configured to align the D-shaped outer perimeter of the transducer housing with the D-shaped cross-section portion of the first lumen as the imaging core is retracted from the catheter assembly.

12. The ultrasonic imaging catheter assembly of claim 8, wherein the second lumen is adapted to house a steering pullwire.

13. A method for maximizing a transducer aperture within a multi-lumen imaging catheter assembly, said method comprising the steps of:

providing an imaging window having a substantially circular cross-section at one end of an elongate tubular element, said substantially circular cross-section of said imaging window having a predetermined internal diameter;

providing a first lumen within said elongate tubular element, said first lumen having a distal end that opens into a cavity defined by an inner wall of said imaging window, said first lumen having one substantially flat wall and having a maximum cross-sectional diameter substantially equal to said internal diameter of said imaging window;

providing a second lumen within at least a portion of said elongate tubular member; and providing an imaging core within said first lumen, said imaging core having a transducer housing with a cross-section corresponding to a cross-section of said first lumen, such that said imaging core is capable of translational movement within said first lumen and rotational movement when extended into said cavity defined by said inner wall of said imaging window.

14. An ultrasonic imaging catheter system comprising:

a substantially tubular element and an imaging window, said imaging window being affixed to a distal end of said tubular element, having a generally circular cross-section and having a predetermined internal cross-sectional diameter, said imaging window having a wall defining an imaging cavity, and said tubular element having a first lumen and a second lumen provided therein, said first lumen being in communication with said imaging cavity, including a first wall having a curvature corresponding to a curvature of said wall of said imaging window, and having a maximum internal cross-sectional diameter substantially equal to said internal cross-sectional diameter of said imaging window;

whereby a housing of an imaging core having a cross-sectional shape corresponding to that of said first lumen may be inserted within said first lumen, passed into said cavity of said imaging window and rotated about a predetermined axis within said imaging window.

15. The ultrasonic imaging catheter system of claim 14, further comprising:

an imaging core having a housing with a cross-sectional shape corresponding to that of said first lumen.

* * * * *

UNITED STATES PATENT AND TRADEMARK OFFICE
CERTIFICATE OF CORRECTION

PATENT NO. : 5,842,994
DATED : December 1, 1998
INVENTOR(S) : Harm TenHoff et al.

It is certified that error appears in the above-identified patent and that said Letters Patent is hereby corrected as shown below:

Column 1, line 41, please change "imagine" to -- imaging --.

Column 3, line 13, please change "that" to -- than --.

Column 12, line 60, please change "potion" to -- portion --.

Signed and Sealed this

Thirteenth Day of June, 2000

*Attest:*

Q. TODD DICKINSON

*Attesting Officer*    *Director of Patents and Trademarks*